(12) United States Patent
Ambroze

(10) Patent No.: US 11,096,704 B2
(45) Date of Patent: Aug. 24, 2021

(54) FECALITH REMOVAL SYSTEM

(71) Applicant: Ellenial Surgical, LLC, Atlanta, GA (US)

(72) Inventor: Wayne Ambroze, Atlanta, GA (US)

(73) Assignee: Ellenial Surgical, LLC, Atlanta, GA (US)

( * ) Notice: Subject to any disclaimer, the term of this patent is extended or adjusted under 35 U.S.C. 154(b) by 436 days.

(21) Appl. No.: 15/978,716

(22) Filed: May 14, 2018

(65) Prior Publication Data

US 2018/0325538 A1 Nov. 15, 2018

Related U.S. Application Data

(60) Provisional application No. 62/505,278, filed on May 12, 2017.

(51) Int. Cl.
*A61B 17/22* (2006.01)
*A61B 17/00* (2006.01)
(Continued)

(52) U.S. Cl.
CPC .. *A61B 17/22031* (2013.01); *A61B 17/00234* (2013.01); *A61B 17/221* (2013.01); *A61B 2017/0034* (2013.01); *A61B 2017/00318* (2013.01); *A61B 2017/00358* (2013.01); *A61B 2017/00398* (2013.01); *A61B 2017/00818* (2013.01); *A61B 2017/2212* (2013.01); *A61B 2017/22037* (2013.01);
(Continued)

(58) Field of Classification Search
CPC .......... A61B 17/221; A61B 2017/2212; A61B 2018/1407; A61B 2018/141; A61B 2017/22037; A61B 2017/00818; A61B 17/22031; A61B 17/22034
See application file for complete search history.

(56) References Cited

U.S. PATENT DOCUMENTS

| | | | |
|---|---|---|---|
| 3,074,408 | A | 1/1963 | Chester |
| 5,776,075 | A | 7/1998 | Palmer |
| (Continued) | | | |

FOREIGN PATENT DOCUMENTS

| | | |
|---|---|---|
| CN | 2676888 Y | 2/2005 |
| WO | WO2016/059210 A1 | 4/2016 |

OTHER PUBLICATIONS

Australian Examination Report No. 1 for Standard Patent Application No. 2018266237 dated Apr. 6, 2020.
(Continued)

*Primary Examiner* — Thomas McEvoy
(74) *Attorney, Agent, or Firm* — Womble Bond Dickinson (US) LLP

(57) ABSTRACT

Disclosed herein is a fecalith treatment system for the removal of an impacted fecalith from a formed diverticula. The fecalith treatment system having an endoscopic device having a steerable line configured to be introduced into a patient via the endoscopic device; and an articulable fecalith treatment device coupled to a distal end of a treatment conduit that is configured to be received therein the steerable line to be delivered to an operative position within the patient. Subsequently, the fecalith treatment device is configured to allow for the removal of the impacted fecalith without damaging the underlying diverticula tissue.

12 Claims, 11 Drawing Sheets

(51) Int. Cl.
*A61B 17/221* (2006.01)
*A61B 17/29* (2006.01)

(52) U.S. Cl.
CPC .............. *A61B 2017/22079* (2013.01); *A61B 2017/2945* (2013.01); *A61B 2017/2947* (2013.01); *A61B 2217/005* (2013.01); *A61B 2217/007* (2013.01)

(56) References Cited

U.S. PATENT DOCUMENTS

| | | | | |
|---|---|---|---|---|
| 5,997,547 | A | * | 12/1999 | Nakao ................... A61B 17/26 606/110 |
| 8,523,879 | B1 | | 9/2013 | Lind et al. |
| 2007/0135820 | A1 | | 6/2007 | Que et al. |
| 2007/0244502 | A1 | | 10/2007 | Deutsch |
| 2011/0004056 | A1 | | 1/2011 | Fischer |
| 2014/0364868 | A1 | | 12/2014 | Dhindsa |
| 2015/0105789 | A1 | * | 4/2015 | Raybin ............ A61B 17/32056 606/113 |
| 2015/0305768 | A1 | * | 10/2015 | Harrah ................ A61B 17/221 606/114 |
| 2016/0174956 | A1 | | 6/2016 | Ciulla et al. |
| 2017/0020550 | A1 | | 1/2017 | Larsen et al. |

OTHER PUBLICATIONS

PCT International Search Report & Written Opinion dated Jul. 10, 2018, which issued for corresponding PCT Application No. PCT/US2018/032537.
Extended European Search Report for related application, EP 18798386.1, dated Dec. 1, 2020.
Australian Examination Report No. 2 for Standard Patent Application No. 2018266237 dated Mar. 29, 2021.

* cited by examiner

FECALITH REMOVAL SYSTEM

CROSS-REFERENCE TO RELATED APPLICATIONS

This application claims the benefit of U.S. Provisional Patent Application No. 62/505,278, filed on May 12, 2017, which is incorporated by reference in its entirety herein and for all purposes.

FIELD OF USE

This invention relates to systems and methods for treating fecaliths disposed anywhere in the intestinal tract but are typically found in the colon. More particularly, the present disclosure relates to systems and methods for removing formed fecaliths that obstruct diverticula.

BACKGROUND

A normal colon is strong and relatively smooth. Small pouches or sacs, called diverticula, can form along the inner lining of the intestine. The presence of these pouches on the colon wall is termed diverticulosis. Although diverticulosis can occur anywhere in the colon, it is most commonly observed in the lower portion of the colon (rectosigmoid region) because the colon is narrowest and the inner pressure is highest in this location. In developed countries, a diet low in fiber increases the risk of diverticulum formation and subsequent diverticulitis. In those countries, diverticula are frequently retained in the left and distal colon, while in Eastern countries, they are more frequently retained in the right colon. Patients with left-sided diverticulosis typically present with left-sided abdominal manifestations of acute or chronic inflammation or bleeding, and the diagnosis is usually made simply on history alone, or is confirmed by the combination of endoscopic and/or radiological investigations. In contrast, complications of right colon diverticulosis may be difficult to diagnose, because of overlap between associated symptoms and signs and those of other right-sided abdominal conditions, particularly in hospitals where the disease is considered uncommon.

Most patients suffering from diverticulitis are elderly, making it difficult to interpret the symptoms and delaying the diagnosis. Diverticula do not possess a muscle layer on their walls, and if not treated, the wall of the diverticulum will gradually thin and may become perforated due to inflammation. After perforation, the lesion might spread to the peritoneal cavity and lead to generalized peritonitis. Occasionally, repeated diverticulitis attacks may lead to fistulization in colon structures and other intestinal segments.

A fecalith, also called a fecaloma or faecaloma, is an extreme form of fecal impaction. A fecalith is a hardening of feces into lumps of varying size and may occur anywhere in the intestinal tract but is typically found in the colon. A fecalith can also obstruct diverticula when they form in the pouches on the colon wall.

Fecaliths impaction in the pouches on the colon wall and attempts at removal can have severe and even lethal effects, such as the rupture of the colon wall by catheter or an acute angle of the fecalith, which can result in stercoral perforation, a condition characterized by the perforation or rupture of the intestine's walls by its internal contents, such as foreign objects, or, more commonly, by hardened feces, i.e., fecaliths, may form in long constipations or other diseases which cause obstruction of transit, such as Chagas disease, Hirschprung's disease, toxic colitis and megacolon. Stercoral perforation is a hazardous, life-threatening situation, as well as a surgical emergency, because the spillage of contaminated intestinal contents into the abdominal cavity leads to peritonitis, a rapid bacteremia with many complications.

It would be desirable to provide a system and method for the efficacious removal of fecaliths from formed diverticula along the inner lining of the intestine.

Further, it would be desirable to have a system and method for the removal of fecaliths from formed diverticula without perforating or otherwise causing damage to the thinned wall of the diverticulum to help prevent the occurrence of generalized peritonitis.

SUMMARY

The disclosure relates to a fecalith treatment system that is configured to allow for the removal of formed fecaliths, such as impacted fecaliths, from formed diverticula without causing harm to the underlying diverticula tissue. In optional aspects, the fecalith treatment system can comprise at least one of an endoscopic device, a light source, an insufflation/irrigation device, a suction catheter, a pressure tank, a valve, and a vacuum pump. The fecalith treatment system further comprises a fecalith treatment device that is configured to remove a fecalith from a diverticula without damaging the underlying tissues of the formed diverticula.

In one aspect, the fecalith treatment device can be conventionally guided via a steerable line portion of the endoscope through the device channel defined in the line portion of the endoscope to a diverticula along the inner lining of the intestine of the patient in which a fecalith is lodged or impacted. The fecalith treatment device described herein can be selectively manipulated by the external operator to gently remove the formed fecalith from the diverticula and, optionally, to capture the removed fecalith for subsequent removal from the patient.

Optionally, the suction catheter can selectively be used to remove any remaining fecalith debris that could be present in the operative field after removal of the fecalith. In a further optional aspect, the insufflation/irrigation device can be used in concert with the fecalith treatment device to aid in gentle urging the fecalith from intimate contact with the underlying diverticula tissue.

Various implementations described in the present disclosure can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

DETAILED DESCRIPTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "layer" includes aspects having two or more layers unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes examples where said event or circumstance occurs and examples where it does not.

The disclosure relates to a fecalith treatment system 10 and method for using same for the removal of calcified fecaliths from formed diverticula along the inner lining of the intestine of the patient.

Figure 1:
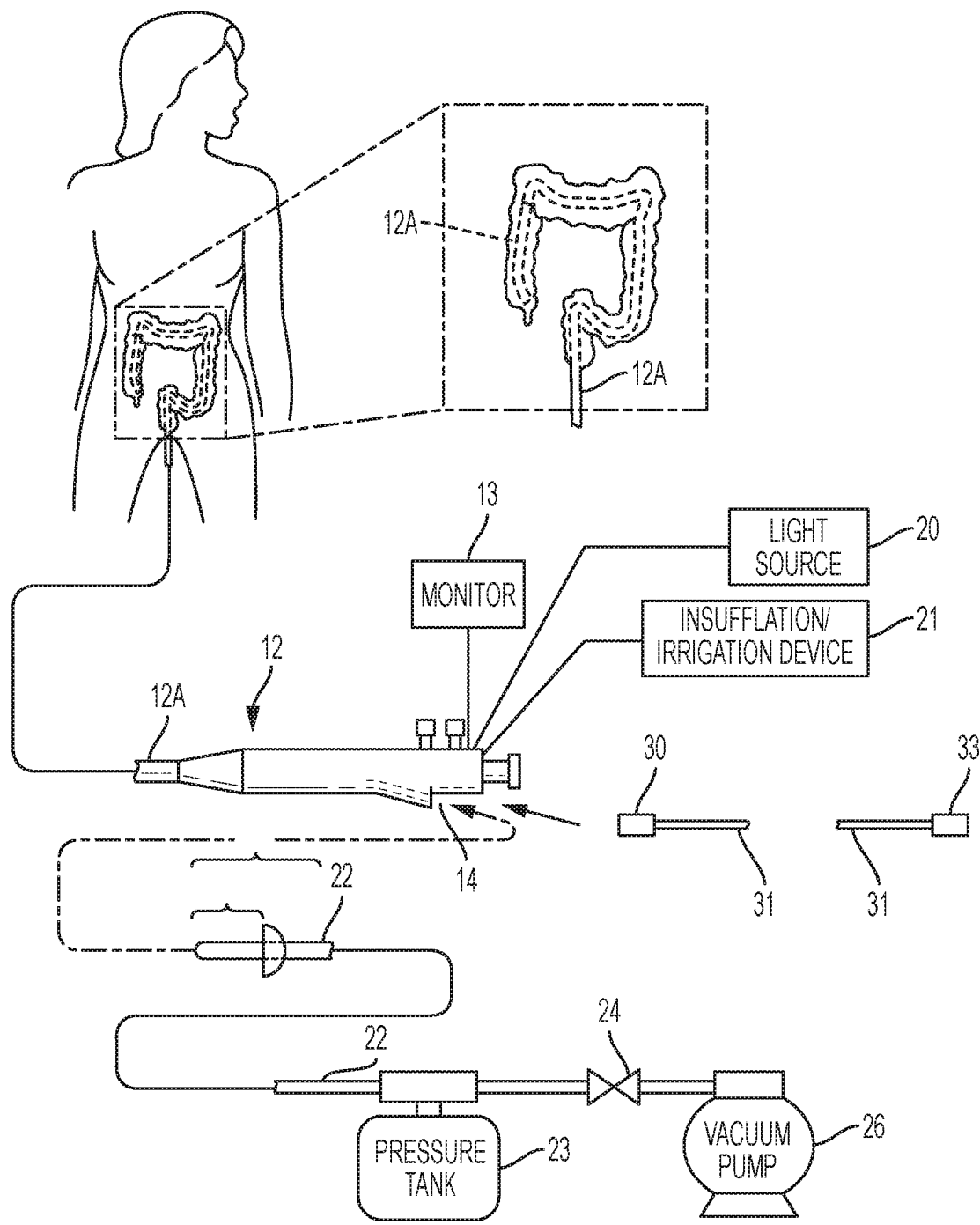
FIG. 1 is a schematic of a fecalith removal system showing an endoscopic device that has a flexible steerable inserting line section that defines a device channel that is configured to receive, via a treatment port, a fecalith treatment device positioned at a distal end of a treatment conduit.
Figure 2:
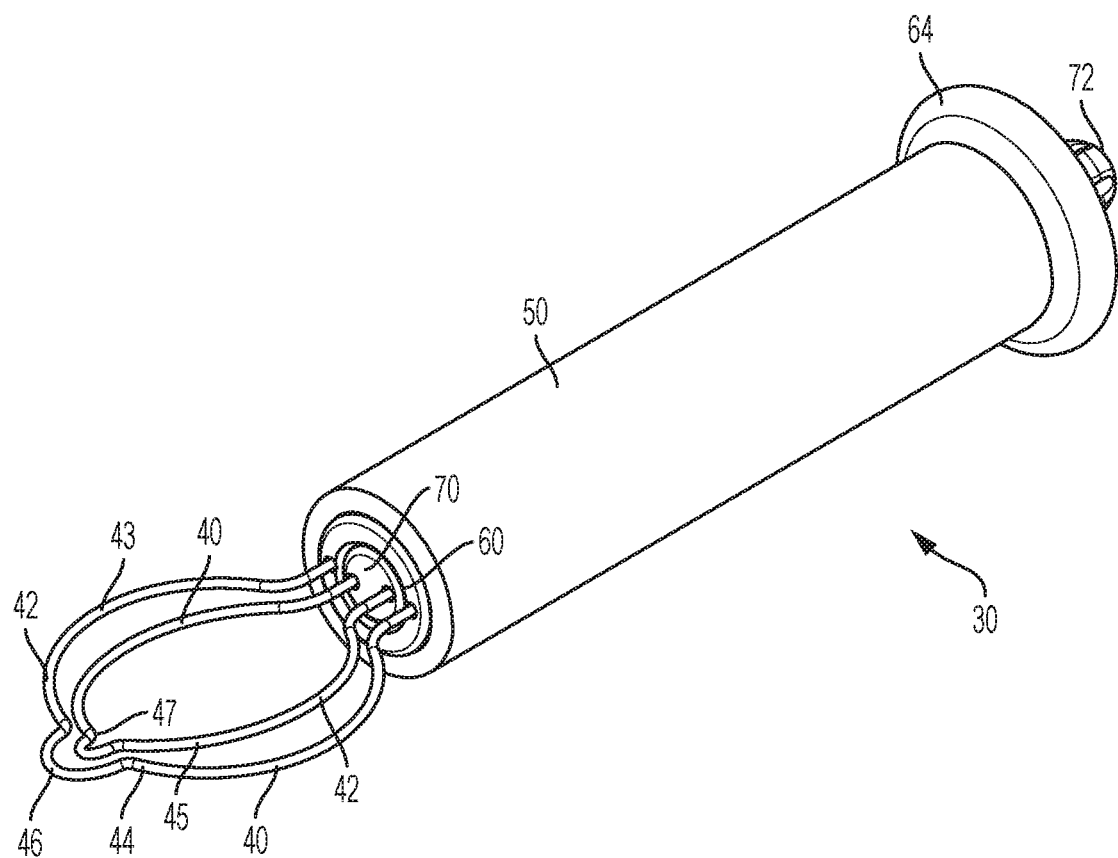
FIG. 2 is a perspective view of a first embodiment of a fecalith treatment device, showing a pair of rotatable loops at the distal end of the fecalith treatment device that are configured to be selectively rotatably articulated about the longitudinal axis of the fecalith treatment device.
Figure 3:
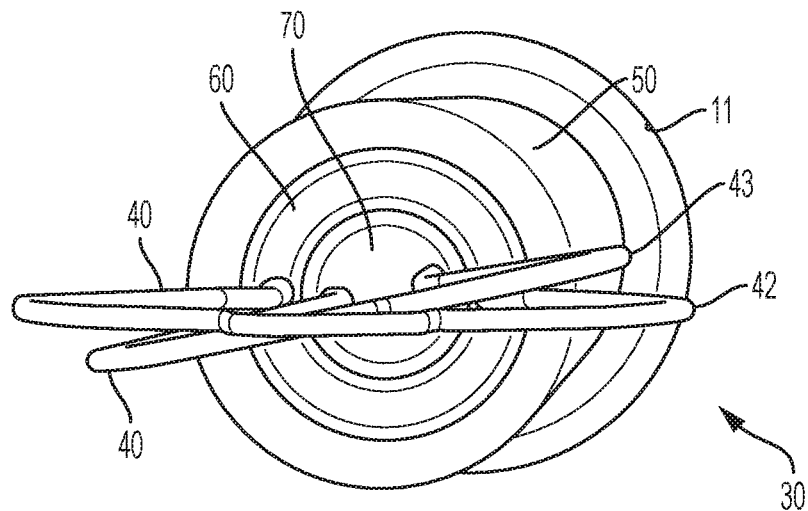
FIG. 3 is an end perspective view of the fecalith treatment device of FIG. 2, showing a pair of rotatable loops at the distal end of the fecalith treatment device.
Figure 4:
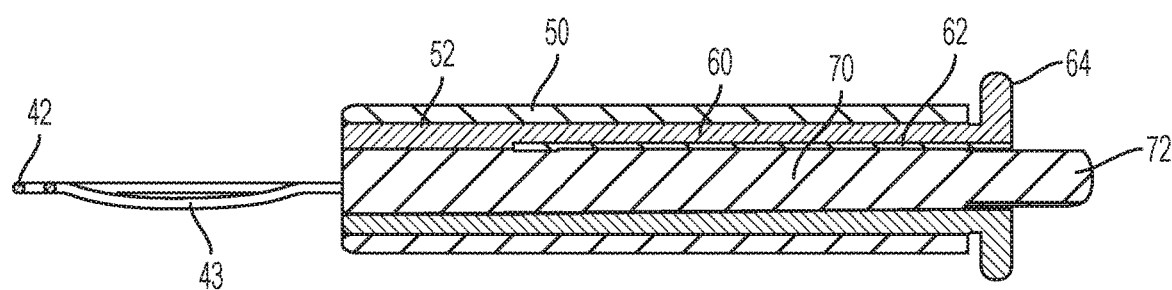
FIG. 4 is a cross-sectional view of the fecalith treatment device of FIG. 2.
Figure 5:
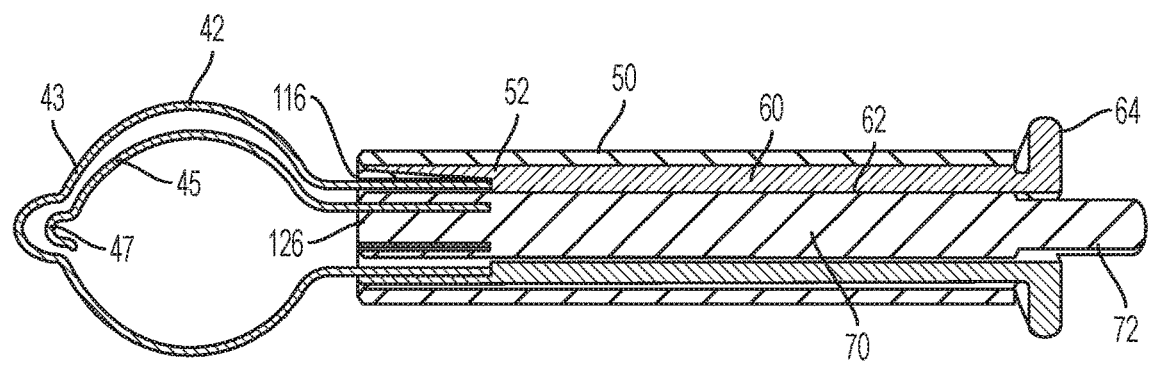
FIG. 5 is a cross-sectional view of the fecalith treatment device of FIG. 2.
Figure 6:
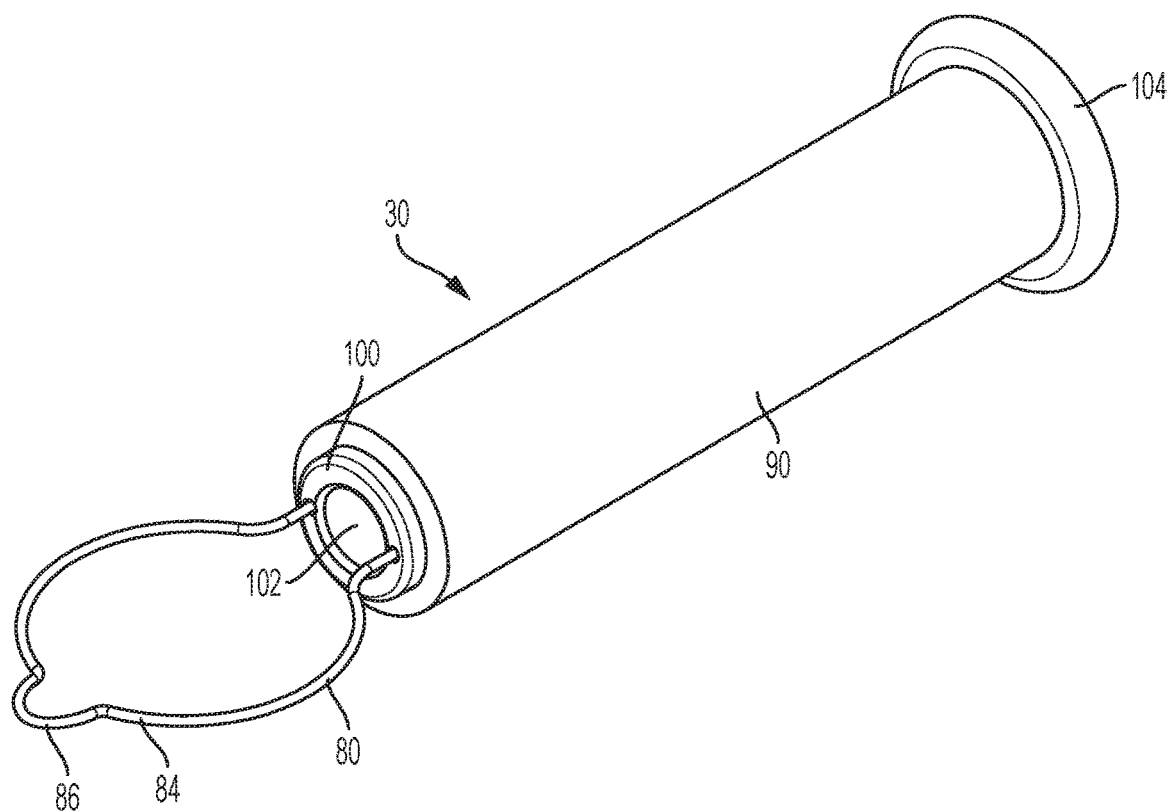
FIG. 6 is a perspective view of a second embodiment of a fecalith treatment device, showing a rotatable loop at the distal end of the fecalith treatment device that is configured to be selectively rotatably articulated about the longitudinal axis of the fecalith treatment device.
Figure 7:
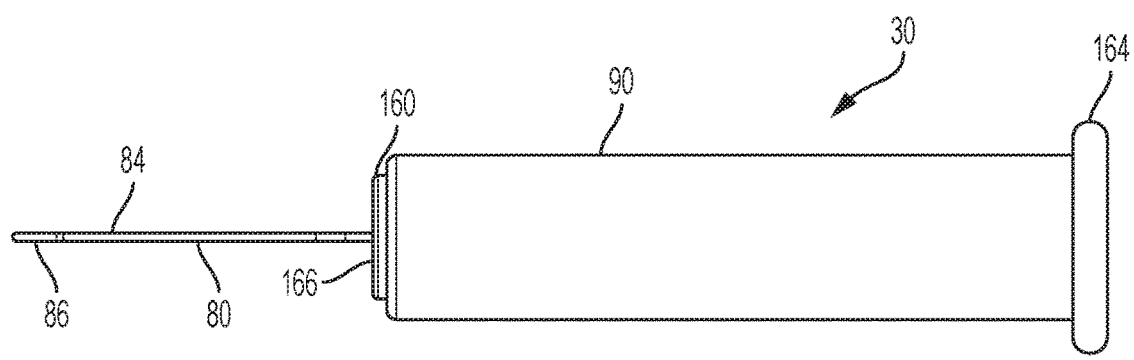
FIG. 7 is a side elevational view of the fecalith treatment device of FIG. 6.
Figure 8:
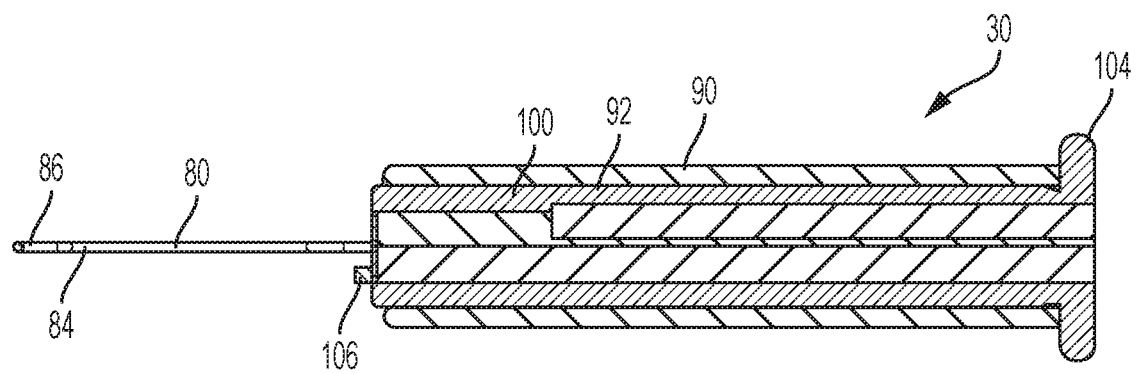
FIG. 8 is a cross-sectional view of the fecalith treatment device of FIG. 6.
Figure 9:
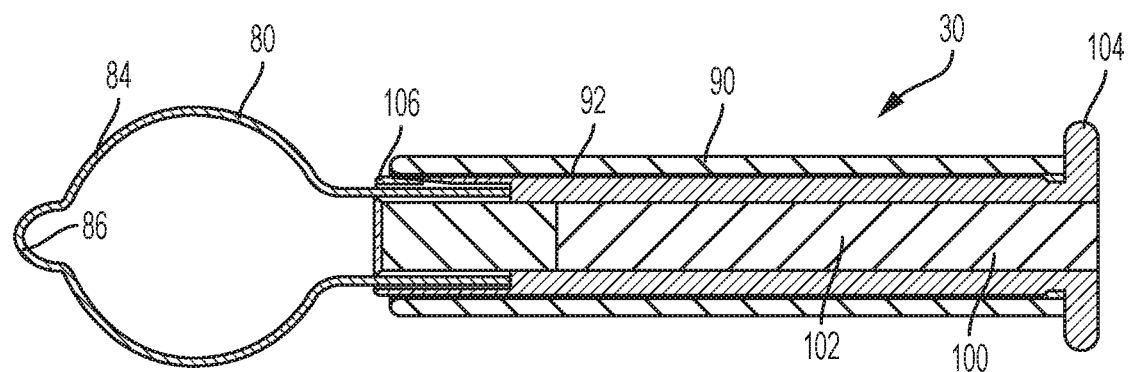
FIG. 9 is a cross-sectional view of the fecalith treatment device of FIG. 6.

As shown in FIG. 1, a fecalith treatment system 10 comprises an endoscopic device 11. The endoscopic device 11 can include a flexible endoscope 12 and a monitor 13. The endoscope 12 has a flexible inserting line 12A that can be selected steered and is configured to be inserted into the colon or large intestine of a subject. The endoscope 12 can display, on the monitor 13, an image captured by an image sensor element provided at the tip end of the inserting line 12A. Various channels (collectively referred to, hereafter, as simply a "channel") for providing various functions required for endoscopic examination and treatment, such as air insufflation, irrigation, and treatment tool insertion, are formed in the inserting line 12A along the axial direction thereof. At least one channel is a device channel that is in communication with an instrument port 14 of the endoscope.

In optional aspects, the fecalith treatment system 10 can further comprise at least one of: a light source 20, an insufflation/irrigation device 21, a suction line 22, a pressure tank 23, a valve (or a connector) 24, and a vacuum pump 26. The pressure tank 23 is connected to the base of the suction line 22 and is in operative fluid communication with the vacuum pump. The valve 24 can be selectively operated to affect the fluid communication between the suction catheter and the vacuum pump. For example, when the valve 24 is open and the vacuum pump 26 is driven to exhaust air, the interior of the suction line 22 can be set to negative pressure of a desired value, and the negative pressure can be selectively maintained.

The fecalith treatment system 10 can further comprise a fecalith treatment device 30 that is configured to remove a fecalith from a diverticula without damaging the underlying tissues of the formed diverticula.

In one aspect, the fecalith treatment device 30 can be conventionally inserted through the instrument port of the endoscope for guidance through the device channel in the line 12a of the endoscope 12 to a diverticula along the inner lining of the intestine of the patient in which a fecalith is lodged or impacted. The insufflation/irrigation device 21 and suction line 22 can also be conventionally guided through respective channels in the inserting line 12a of the endoscope 12 to the diverticula. In optional aspects, the fecalith treatment device 30 can be mounted at the tip end of the insufflation/irrigation device 21, the tip end of the suction line 22, or can mounted to a distal end of a treatment conduit 31 that can be introduced via the same or a separate channel from the suction catheter 22 and/or the insufflation/irrigation device 21.

In one aspect, the operator can insert the tip section of the endoscope 12 from the anus of the patient and into the desired operative position. After observation, if a fecalith is observed in a diverticula, the fecalith can be removed though the use of the fecalith treatment device 30 described below that is coupled to at least one conventional operational handle 33 without harming or puncturing the underlying diverticula tissues. Optionally, the suction catheter 22 can selectively be used to remove any remaining fecalith debris that could be present in the operative field after removal of the fecalith. In a further optional aspect, the insufflation/irrigation device 21 can be used in concert with the fecalith treatment device 30 to aid in gentle urging the fecalith from intimate contact with the underlying diverticula tissue.

Referring now to FIG. 2-5, in a first embodiment, the fecalith treatment device 30 can comprise a pair of rotatable loops 40 that can be positioned at the distal end of the fecalith treatment device. In this aspect, it is contemplated that the pair of rotatable loops 40 can be configured to be selectively and rotatably articulated about the longitudinal axis of the fecalith treatment device. In this aspect, the fecalith treatment device 30 can comprise an elongate hollow cylindrical body 50 extending along a longitudinal axis and defining a first interior cavity 52, a first elongate drive member 60 that configured to be rotatably mounted about the longitudinal axis therein the interior cavity 52 of the cylindrical body 50, and a second elongate drive member 70 that is configured to be independently rotated about the longitudinal axis and relative to the first elongate drive member 60.

In this aspect, the first elongate drive member 60 is cylindrical and defines a second interior cavity 62. The proximal end of the first elongate drive member defines a transversely extending lip 64 that extends transversely away from the longitudinal axis. The lip 64 can be articulated for rotative movement of the first elongate drive member relative to the cylindrical body 50. Similarly, the second elongate drive member 70 is configured to the rotatably received within the second interior cavity 62 and has a proximal end 72 that extends proximally beyond the transversely extending lip 64 of the first elongate drive member 60 to allow for independent selective rotative and/or axial movement of the second elongate drive member 70 relative to the first elongate drive member 60.

A first loop 42 of the pair of rotatable loops 40 is coupled to a distal end 66 of the first elongate drive member 60 and extends distally longitudinally a first distance away from the distal end 66 of the first elongate drive member in an first operative plane that is substantially parallel to the longitudinal axis of the cylindrical body. In one aspect, it is contemplated that the respective loop ends of the first loop 42 will be mounted to the distal end 66 of the first elongate drive member and will be spaced in opposition about 180 degrees from each other such that the first loop is positioned in the first operative plane that bisects the longitudinal axis. The distal portion 44 of the first loop can have a smooth, continuously curved shape that is configured to not injure or otherwise damage delicate diverticula tissues. It is contemplated that at least a distal portion of the first loop can be configured to yield to the diverticula tissue wall at the operative location. Optionally, the exposed portions of the first loop can be configured to yield to the diverticula tissue wall at the operative location. It is contemplated that the first loop can have a width, transverse to the longitudinal axis of the first elongate drive member that exceeds the diameter of the impacted fecalith. In a further option, and as illustrated, the distal portion 44 of the first loop can define a gentle distally oriented tip 46 that can help to dislodge an impacted fecalith without damaging the underlying diverticula tissues. In this aspect, the tip 46 would be configured to yield to the diverticula tissue wall at the operative location.

Similarly, a second loop 43 of the pair of rotatable loops 40 is coupled to a distal end 76 of the second elongate drive member 70 and extends distally longitudinally a second distance from the distal end 76 of the second elongate drive member. In one aspect, the second distance is less than the first distance to help prevent undesired binding contact between the respective first and second loops 42, 43. In one aspect, it is contemplated that the respective loop ends of the second loop 43 will be mounted to the distal end 76 of the second elongate drive member and will be spaced in opposition about 180 degrees from each other such that the second loop is positioned in a second operative plane that bisects the longitudinal axis. The distal portion 45 of the second loop can have a smooth, continuously curved shape that is configured to not injure or otherwise damage delicate diverticula tissues. It is contemplated that at least a distal portion of the second loop can be configured to yield to the diverticula tissue wall at the operative location. Optionally, the exposed portions of the second loop can be configured to yield to the diverticula tissue wall at the operative location. It is further contemplated that the second loop can have a width, transverse to the longitudinal axis of the first elongate drive member that exceeds the diameter of the impacted fecalith but is less than the operative diameter of the first loop. In a further option, and as illustrated, the distal portion 45 of the second loop can define a gentle distally oriented tip 47 that can help to dislodge an impacted fecalith without damaging the underlying diverticula tissues. In this aspect, the tip 47 would be configured to yield to the diverticula tissue wall at the operative location.

In operation, the respective first and second elongate drive members can be rotated relative to each other so that the operative first and second planes of the respective first and second loops 42, 43 can be moved relative to each other. As shown, the respective first and second loops can be selectively positioned such that the operative first and second planes can be substantially or proximately co-planer, which is a preferred position for gently urging the impacted fecalith away from the underlying diverticula tissues. As one skilled in the art will appreciate, the respective first and second loops can also be selectively positioned such that the operative first and second planes can be positioned substantially or proximately transverse to each other, which is a preferred position for capturing the fecalith matter upon separation from the underlying diverticula tissues.

Further, is it contemplated that one or both of the respective first and second elongate drive members 60, 70 can be moved axially relative to the cylindrical body 50. One skilled in the art will appreciate that proximal movement of one or both of the respective first and second elongate drive members 60, 70 relative to the distal end 54 of the cylindrical body 50 will result in concurrent proximal axial movement of one or both of the respective first and second loops 42, 43 relative to the distal end 54 of the cylindrical body 50, which will result in the reduction of the effective operative diameters of the first and second loops 42, 43 and can aid in securing the captured fecalith.

In operation, the distal portions of the first and second loops 42, 43 can be positioned at the luminal opening of the diverticulum containing the fecalith. The respective first and second wire loops can then be advanced into the diverticulum around the fecalith with, for example, the respective first and second loops being exemplarily selectively positioned such that the operative first and second planes of the first and second loops can be substantially or proximately co-planer, and the second loop 43 can subsequently be rotated relative to the first loop 42 around and about the fecalith. This relative rotation of the second loop relative to the first loop can be between about 0 degrees to about 180 degrees and in one preferred aspect, to between about 80 degrees to about 110 degrees, and in a further aspect, to about 90 degrees. The first and second loops 42, 43 with the fecalith constrained within, can then be retracted into the lumen of the bowel. Subsequently, the first and second loops 42, 43 can be articulated to or towards a position in which the operative first and second planes of the first and second loops can be substantially or proximately co-planer, which allows the fecalith to be released or disposed into the lumen of the bowel so it can be expelled with other fecal matter.

Referring now to FIG. 6-9, in a second embodiment, the fecalith treatment device 30 can comprise a rotatable loop 80 that is positioned at the distal end of the fecalith treatment device. In this aspect, the rotatable loop 80 is configured to be selectively and rotatably articulated about the longitudinal axis of the fecalith treatment device. In this aspect, the fecalith treatment device 30 can comprise an elongate hollow cylindrical body 90 extending along a longitudinal axis and defining a first interior cavity 92 and an elongate drive member 100 that configured to be rotatably mounted about the longitudinal axis therein the first interior cavity 92 of the cylindrical body 90.

In this aspect, the elongate drive member 100 is cylindrical and defines a second interior cavity 102. The proximal end of the first elongate drive member defines a transversely extending lip 104 that extends transversely away from the longitudinal axis that can be articulated for rotative movement of the elongate drive member 100 relative to the cylindrical body 90.

The rotatable loop 80 is coupled to a distal end 106 of the elongate drive member 100 and extends distally from the distal end 106 of the elongate drive member. In one aspect, it is contemplated that the respective loop ends of the loop 80 will be mounted to the distal end 106 of the elongate drive member and will be spaced in opposition about 180 degrees from each other such that the loop 80 can be positioned in a plane that bisects the longitudinal axis. It is contemplated that the distal portion 84 of the loop 80 can have a smooth, continuously curved shape that is configured to not injure or otherwise damage delicate diverticula tissues. Optionally, and as illustrated, the distal portion 84 of the loop 80 can define a gentle distally oriented tip 86 that can help to dislodge an impacted fecalith without damaging the underlying diverticula tissues. It is further contemplated that at least a distal portion of the loop 80 can be configured to yield to the diverticula tissue wall at the operative location. Optionally, the exposed portions of the second loop can be configured to yield to the diverticula tissue wall at the operative location.

In operation, the elongate drive member 100 can be rotated relative to the cylindrical body 90 to aid in gently inserting the distal portion of the loop 80 into luminal opening of the diverticulum to allow for the further introduction of the loop through the luminal opining and into contact with the impacted fecalith without damaging the underlying diverticula tissues. Further, is it contemplated that the elongate drive member 100 can be moved axially relative to a distal end 94 of the cylindrical body 90. One skilled in the art will appreciate that proximal movement of the elongate drive member 100 relative to the distal end 94 of the cylindrical body 90 will result in concurrent proximal axial movement of the loop 80, which will result in the reduction of the effective operative diameter of the loop 80 and can aid in both the introduction of the loop 80 through the luminal opening and in securing the captured fecalith.

For example, the distal portion 84 of the loop 80 can be positioned at the luminal opening of the diverticulum containing the fecalith and subsequently advanced into the diverticulum around the fecalith. The loop 80 can be selectively rotated to gently urge the separation of the fecalith from the delicate underlying tissue. Upon separation of the fecalith from the underlying tissue, the loop can further be used to urge the fecalith into the lumen of the bowel for expulsion with other fecal matter via normal physical bowel action. Alternatively, the fecalith can be secured by the axial movement of the elongate drive member 100 relative to the cylindrical body 90, which results in the constriction of the operative diameter of the loop 80. Subsequently, the loop 80, with the secured fecalith, can be withdrawn into the lumen of the bowel. In this aspect, movement of the elongate drive member 100 relative to the cylindrical body 90 can provide for the expansion of the operative diameter of the loop 80 and subsequently disposition of the fecalith into the lumen of the bowel so it can be expelled with other fecal matter.

Referring to FIGS. 10-16, in a third embodiment, the fecalith treatment device 30 can comprise a plurality of leaves 160 at the distal end of the fecalith treatment device that are configured to selectively articulate about and between an open position and the illustrated closed position. In this aspect, the fecalith treatment device 30 can comprise an elongate hollow cylindrical body 132 extending along a longitudinal axis and defining an interior cavity 136, a cap member 150 that is fixedly seated at the distal end of the cylindrical body 132, and a plug member 140 that is inserted and fixed in a proximal portion of interior cavity 136.

In one aspect, the cap member 150 has a post 152 that extends distally from a distal end of the cylindrical body 132 coaxial to the longitudinal axis. Two pairs of pin mounts 154 extend outwardly from the post 152 substantially transverse to the longitudinal axis. It is contemplated the one pair of pin mounts 154 will extend along a first common axis, transverse to the longitudinal axis, from either side of the post 152 and the other pair of pin mounts 154 will extend along a second common axis, transverse to the longitudinal axis and spaced longitudinally from the first common axis, from either side of the post 152. In another aspect, it is contemplated that the cap member 150 will define a plurality of spaced bores 155 that extend longitudinally through the cap member and that are sized and shaped for operative receipt of the articulation guide wires. It one exemplary aspect, the bores 155 are equidistantly spaced from each other.

Each leaf 160 of the plurality of leaves 160 has a distal spoon member 162 that has an outer surface 64 and an inner concave surface 163. Each leaf 160 also has an actuation member 170 that has a distal end 172 that is integrally coupled to a proximal end portion 166 of the distal spoon member 162, a proximal end 174 that is configured to be coupled to an articulation guide wire [not shown] and a middle portion 176 that defines a bore that is sized and shaped to be received on one pin mount 154. Each leaf 160 is rotatably mounted to a respective pin mount 54 and is secured thereto by the mounting of pin end caps 158 on each pin mount.

Figure 10:
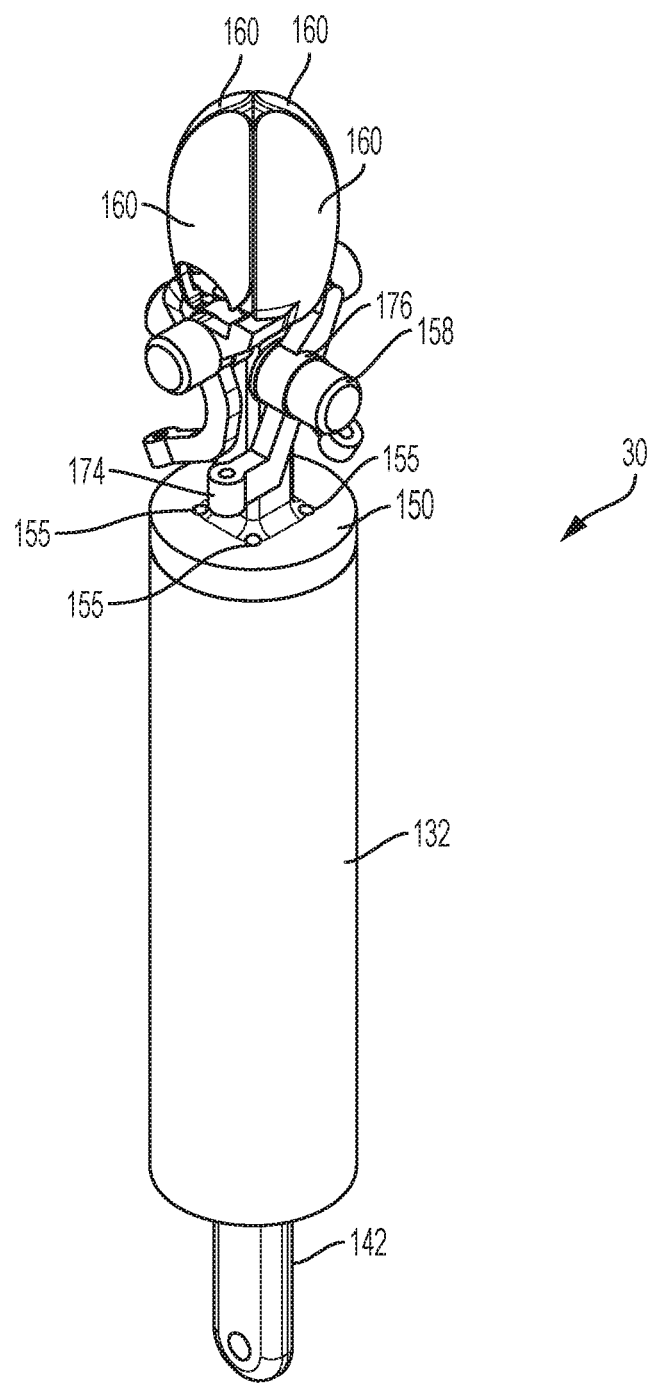
FIG. 10 is a perspective view of a third embodiment of a fecalith treatment device, showing a plurality of leaves at the distal end of the fecalith treatment device that are configured to be selectively articulate between an open position and the illustrated closed position.
Figure 11:
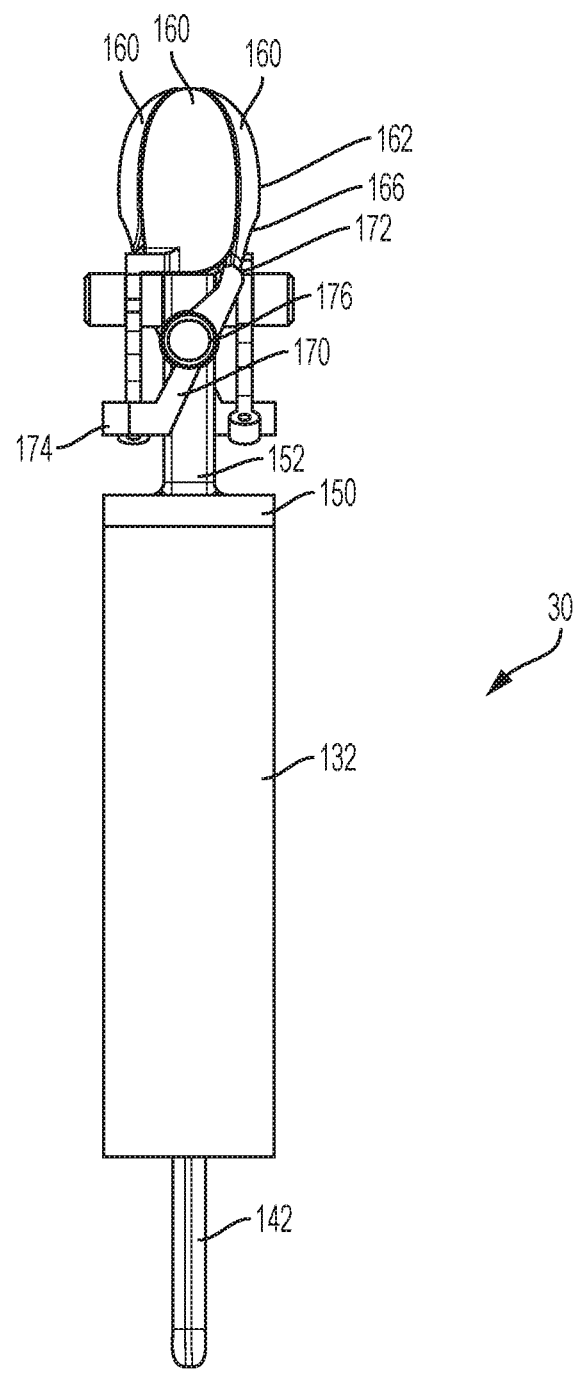
FIG. 11 is a side elevational view of the fecalith treatment device of FIG. 10.
Figure 12:
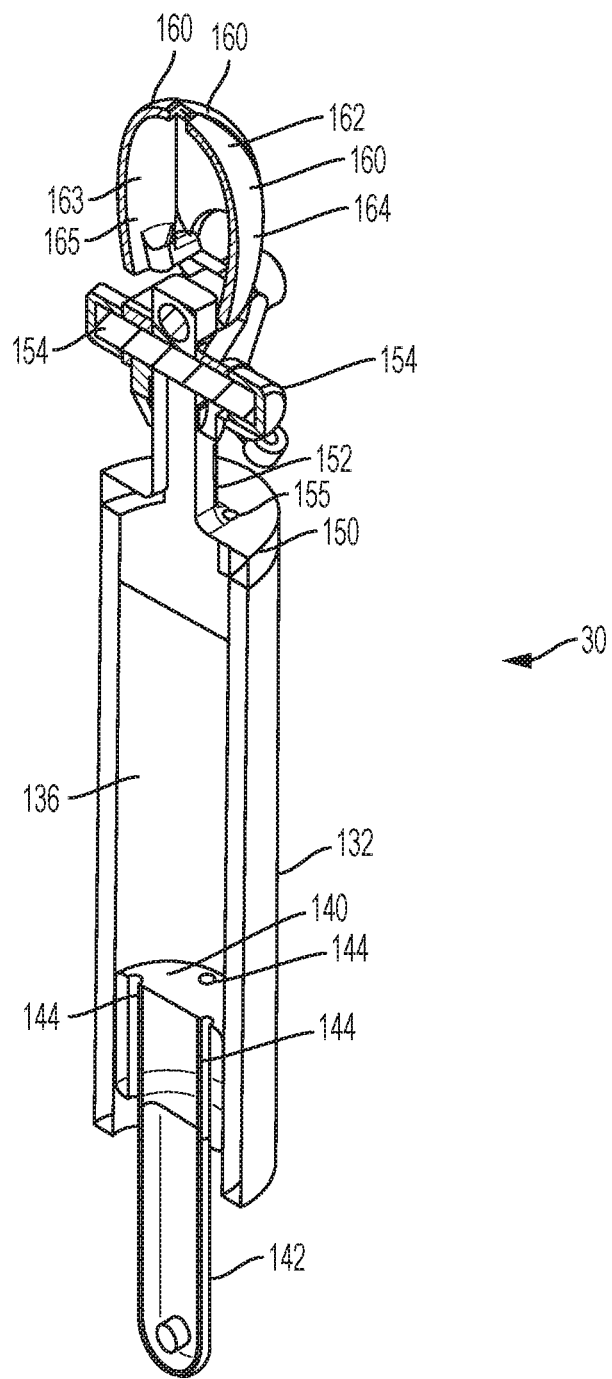
FIG. 12 is a cross-sectional view of the fecalith treatment device of FIG. 10, showing defined channels in the fecalith treatment device for guidewires that are configured to couple to the proximal ends of the plurality of leaves.
Figure 13:
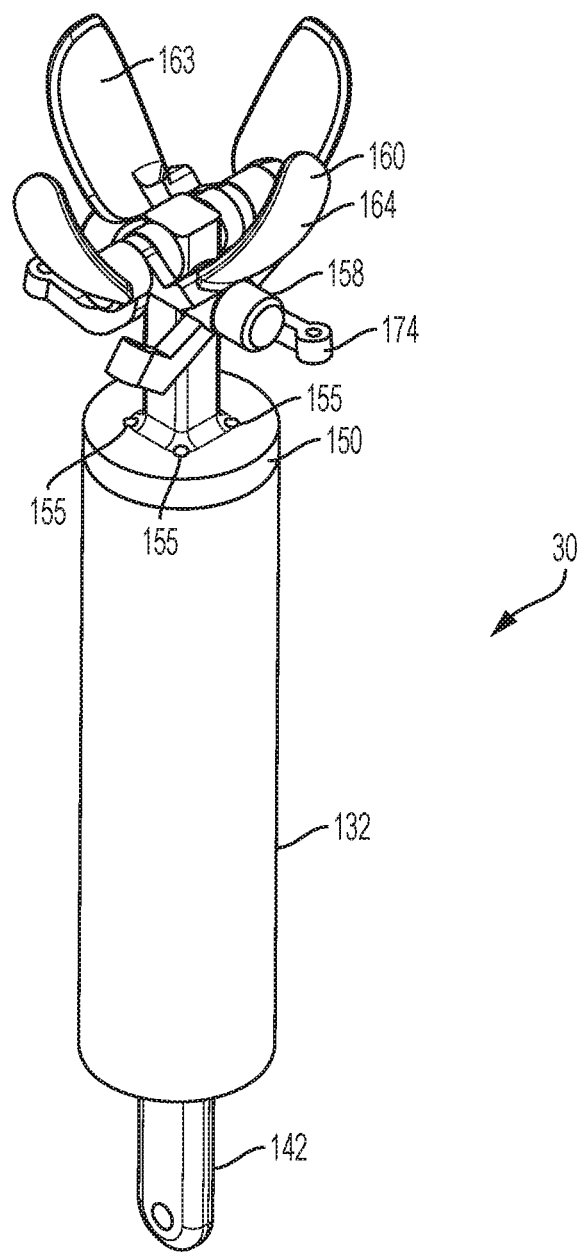
FIG. 13 is a perspective view of the fecalith treatment device of FIG. 10, showing the plurality of leaves at the distal end of the fecalith treatment device in the open position.
Figure 14:
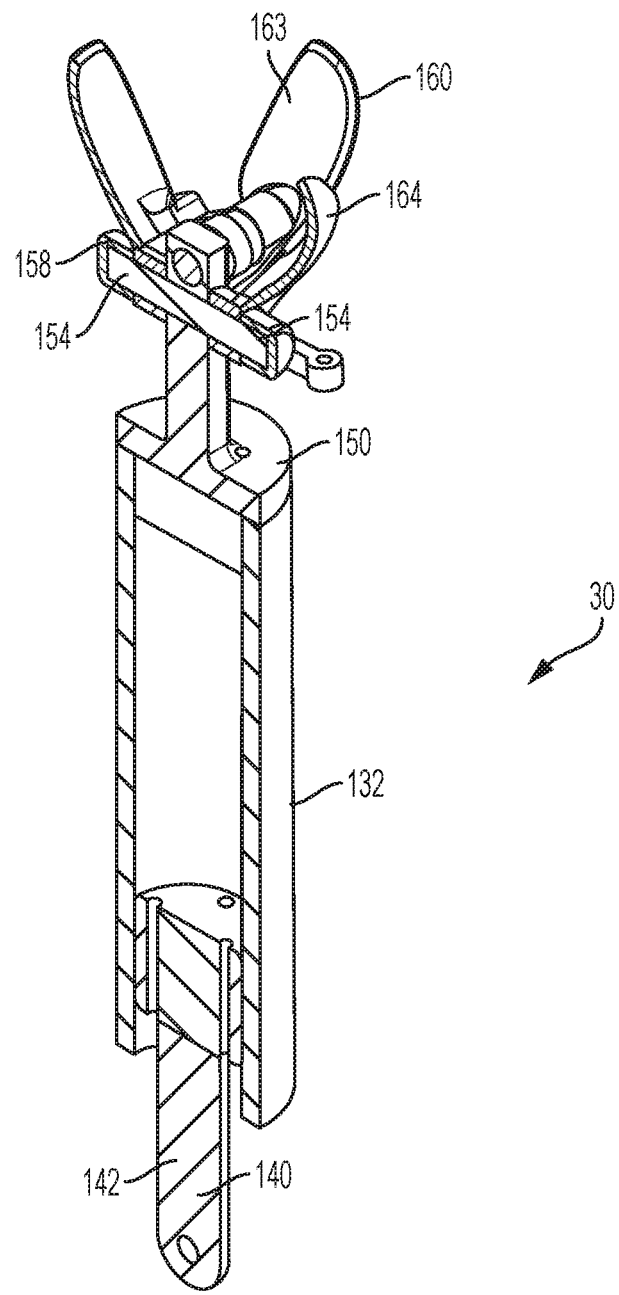
FIG. 14 is a cross-sectional view of the fecalith treatment device of FIG. 13, showing defined bores in a cap member and a plug member of the fecalith treatment device for movable receipt of articulation guide wires that are configured to couple to the proximal ends of the plurality of leaves for the selective rotative movement of the plurality of leaves.
Figure 15:
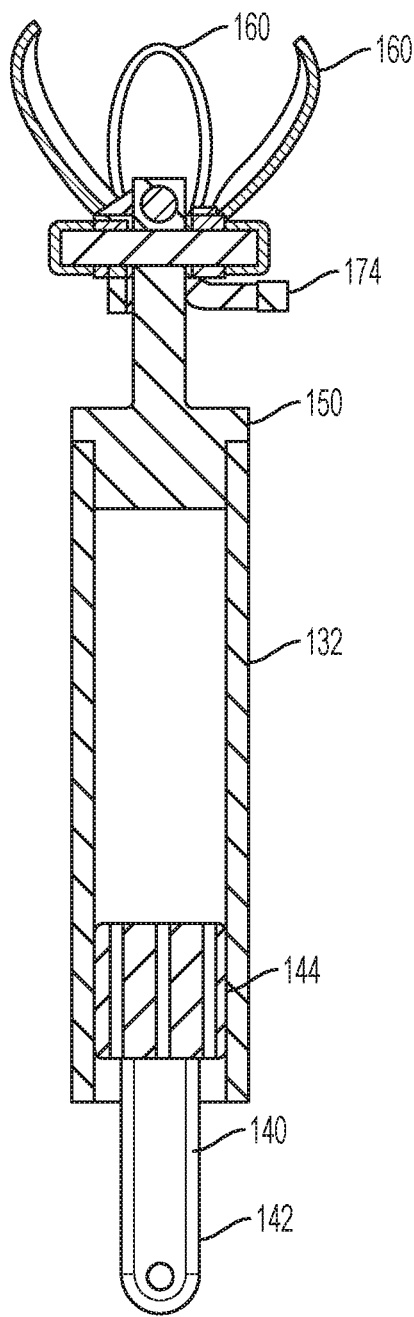
FIG. 15 is a side elevational view of the fecalith treatment device of FIG. 13.
Figure 16:
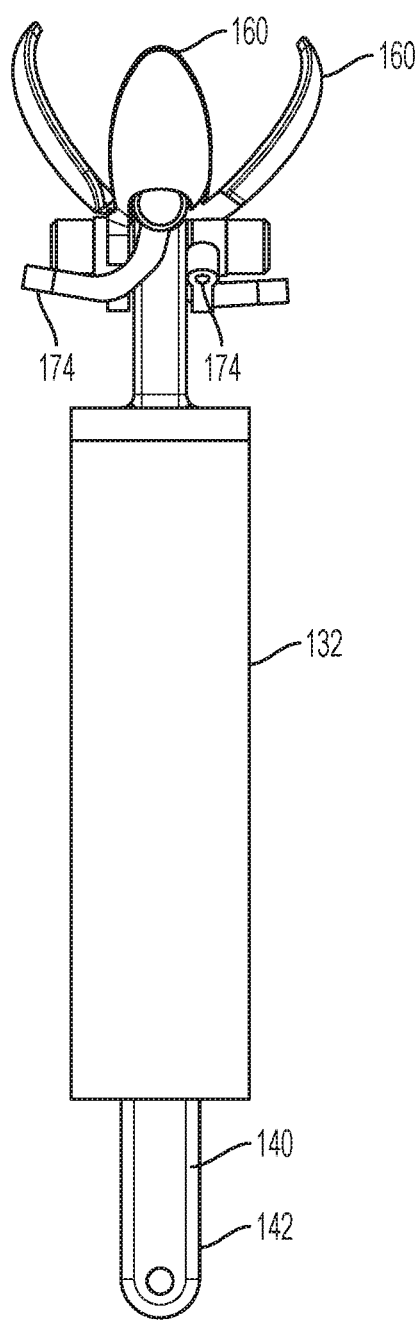
FIG. 16 is a cross-sectional view of the fecalith treatment device of FIG. 14.

As shown in FIG. 10, when the plurality of leaves 160 is in the closed position, the actuation member 170 can be positioned at an angle with respect to the longitudinal axis of the cylindrical body 132 with the respective distal and proximal ends 172, 174 being positioned offset from each other on opposing sides of a plane bisecting the longitudinal axis and the respective pin mount 154 that the leaf 160 is mounted thereon. One skilled in the art will appreciated that this allows the leaf 160 to be selectively rotated about the pin mount 154 upon the selective application of force onto the proximal end 174 of the actuation member 170 via operator force applied to the articulation guide wire via operator force applied to a select operational handle 33.

As illustrated, it is contemplated the spoon member 162 will have a curved shape when viewed in cross-section relative to a plane bisecting the longitudinal axis and when viewed in cross-section relative to a plane that is substantially transverse to the longitudinal axis. The outer surface 164 of the respective plurality of leaves 160 defines a substantially smooth curved shape that is configured to not injure or otherwise damage the delicate underlying diverticula tissues. In the closed position, the plurality of leaves defines an interior void 165 that is configured to at least partially contain or otherwise secure a recovered fecalith and the outer surfaces 164 of the respective plurality of leaves 160 form a curved bulb shape that is configured to not injure or otherwise damage the underlying diverticula tissues.

The plug member 140 has an elongate mounting member 142 that extends along the longitudinal axis and proximally away from the cylindrical body 132. In this aspect, the elongate mounting member is configured to be mounted to the distal tip end of the conduit 31. In another aspect, it is contemplated that the plug member 140 will define a plurality of spaced bores 44 that extend longitudinally through the plug member and that are sized and shaped for operative receipt of the articulation guide wires. In one exemplary aspect, the bores 44 are equidistantly spaced from each other.

In operation, the distal end of the fecalith treatment device 30 can be placed into the diverticular opening containing the fecalith and the plurality of leaves 160 can be selectively articulated between the closed position to the open position so that the fecalith or at least portions of the fecalith can be positioned therein the interior void 165, after which the plurality of leaves 160 are selectively articulated between from the open position to or toward the closed position such that the fecalith or at least portions of the fecalith is secured therein the interior void 165 defined by the plurality of leaves. Alternatively, the distal end of the fecalith treatment device 30 can be placed into the diverticular opening containing the fecalith and the plurality of leaves 160 can be selectively articulated about and between the open position and the open position so that the fecalith or at least portions of the fecalith can be grasped by portions of the plurality of leaves 160. Thus, in either exemplary methods, the fecalith can be selectively removed from the diverticulum either in its entirety or in piecemeal fashion. It is further contemplated that, once the fecalith matter is removed from the diverticulum into the bowel lumen, it can be expelled with other fecal matter via normal physical bowel action.

It should be appreciated that diverticulitis is associated with significant morbidity and mortality in the developed world. Recent data suggest that acute and chronic diverticulitis contributes to over 300,000 hospital admissions, with over 2 million outpatient visits and an estimated $2.4 billion in healthcare cost in the United States each year. Despite its significant morbidity, the pathophysiology of diverticulitis remains elusive and understudied. Epidemiological data indicates that 10% of patients found to have diverticulosis on colonoscopy develop diverticulitis. It is postulated that the pathological mechanism inciting diverticular disease is the in-situ formation of fecaliths within formed diverticula, causing obstruction and anaerobic overgrowth or ulceration which can lead to micro-perforation and clinical diverticulitis.

An initial trail by the inventor has demonstrated that patients with diverticulosis that had fecaliths showed a 48% incidence of being treated for diverticulitis in the past versus 12% in those who did not have fecaliths. Further endoscopic trail retrievals of fecaliths has proven its preventative potential as successful retrieval, defined as complete removal of fecaliths from the diverticula, was seen in 85% of cases performed by an experienced endoscopist. No increase in the incidence of perforations or clinically significant bleeding was seen in the trials.

It should be emphasized that the above-described embodiments are merely possible examples of implementations, merely set forth for a clear understanding of the principles of the present disclosure. Many variations and modifications can be made to the above-described embodiment(s) without departing substantially from the spirit and principles of the present disclosure. All such modifications and variations are intended to be included herein within the scope of the present disclosure, and all possible claims to individual embodiments or combinations of elements or steps are intended to be supported by the present disclosure. Moreover, although specific terms are employed herein, as well as in the claims which follow, they are used only in a generic and descriptive sense, and not for the purposes of limiting the described invention, nor the claims which follow.

What is claimed is:

1. A fecalith treatment system for the removal of an impacted fecalith from a formed diverticula without damaging the underlying diverticula tissue, comprising:
an endoscopic device comprising a steerable line configured to be introduced into a patient, the endoscopic device having an instrument port in communication with a device channel defined within the steerable line that extends to a distal end of the steerable line;
a fecalith treatment device coupled to a distal end of a treatment conduit, the fecalith treatment device configured to be received through the instrument port and the device channel of the endoscopic device, the fecalith treatment device comprising:
an elongate hollow cylindrical body extending along a longitudinal axis of the cylindrical body and defining a first interior cavity,
a first elongate drive member configured to be rotatably mounted about a longitudinal axis of the first interior cavity of the cylindrical body, the first elongate drive member defining a second interior cavity;
a second elongate drive member configured to be rotatably mounted about a longitudinal axis of the second interior cavity, wherein the second elongate drive member is configured to be independently rotated about the longitudinal axis of the cylindrical body and relative to the first elongate drive member; and a pair of rotatable loops configured to be selectively and rotatably articulated about a longitudinal axis of the cylindrical body, wherein a first loop of the pair of rotatable loops is coupled to a distal end of the first elongate drive member and extends distally longitudinally a first distance away from the distal end of the first elongate drive member in an first operative plane that is substantially parallel to the longitudinal axis of the cylindrical body, wherein a second loop of the pair of rotatable loops is coupled to a distal end of the second elongate drive member and extends distally longitudinally a second distance from the distal end of the second elongate drive member in a second operative plane, wherein the second distance is less than the first distance, wherein the entirety of each of the first and second loops is configured to yield to a diverticula tissue wall at an operative location to not injure or otherwise damage the diverticula tissue, and wherein distal portions of the respective first loop and second loop have a smooth, continuously curved shape that is configured to not injure or otherwise damage the diverticula tissue.

2. The fecalith treatment system of claim 1, wherein the first elongate drive member has a proximal end that defines a transversely extending lip that extends transversely away from the longitudinal axis of the second interior cavity, wherein the lip is configured to be articulated for rotative movement of the first elongate drive member relative to the cylindrical body 50.

3. The fecalith treatment system of claim 2, wherein the second elongate drive member has a proximal end that extends proximally beyond the lip of the first elongate drive member to allow for independent selective rotative and/or axial movement of the second elongate drive member relative to the first elongate drive member.

4. The fecalith treatment system of claim 1, wherein respective loop ends of the first loop are mounted to the distal end of the first elongate drive member and are spaced in opposition about 180 degrees from each other.

5. The fecalith treatment system of claim 1, wherein the distal portion of the first loop defines a gentle distally oriented tip configured to dislodge an impacted fecalith without damaging the underlying diverticula tissue.

6. The fecalith treatment system of claim 5, wherein the tip is configured to yield to the diverticula tissue wall at the operative location.

7. The fecalith treatment system of claim 1, wherein respective loop ends of the second loop are mounted to the distal end of the second elongate drive member and are spaced in opposition about 180 degrees from each other.

8. The fecalith treatment system of claim 1, wherein the distal portion of the second loop can define a gentle distally oriented tip configured to dislodge an impacted fecalith without damaging the underlying diverticula tissue.

9. The fecalith treatment system of claim 8, wherein the tip is configured to yield to the diverticula tissue wall at the operative location.

10. The fecalith treatment system of claim 1, wherein the respective first and second elongate drive members are configured to be rotated relative to each other so that the operative first and second planes of the respective first and second loops are movable relative to each other.

11. The fecalith treatment system of claim 10, wherein the first loop has a selectable width, transverse to the longitudinal axis of the second interior cavity, wherein the second loop has a selectable width, transverse to the longitudinal axis of the second interior cavity, and wherein the selectable width of the second loop is less than the width of the first loop.

12. The fecalith treatment system of claim 1, wherein one or both of the respective first and second elongate drive members are configured to move axially relative to the cylindrical body to effect the selection of the width of the respective first and second loops.

* * * * *